United States Patent
Wen et al.

(10) Patent No.: US 12,380,978 B2
(45) Date of Patent: Aug. 5, 2025

(54) REMOTE CONCURRENT ASSESSMENT OF FUNCTIONAL MOBILITY AND WORKING MEMORY

(71) Applicant: INTERNATIONAL BUSINESS MACHINES CORPORATION, Armonk, NY (US)

(72) Inventors: Bo Wen, New York, NY (US); Erhan Bilal, Westport, CT (US); Jenna Reinen, Rye Brook, NY (US)

(73) Assignee: International Business Machines Corporation, Armonk, NY (US)

( * ) Notice: Subject to any disclaimer, the term of this patent is extended or adjusted under 35 U.S.C. 154(b) by 238 days.

(21) Appl. No.: 18/311,924

(22) Filed: May 4, 2023

(65) Prior Publication Data
US 2024/0371484 A1 Nov. 7, 2024

(51) Int. Cl.
G16H 20/00 (2018.01)
G16H 40/67 (2018.01)
G16H 50/20 (2018.01)

(52) U.S. Cl.
CPC ............. G16H 20/00 (2018.01); G16H 40/67 (2018.01); G16H 50/20 (2018.01)

(58) Field of Classification Search
CPC ........ G16H 20/00; G16H 40/67; G16H 50/20; G16H 50/30
See application file for complete search history.

(56) References Cited

U.S. PATENT DOCUMENTS

| | | | |
|---|---|---|---|
| 8,764,532 B1 | 7/2014 | Berme | |
| 11,217,033 B1* | 1/2022 | Morgan | G16H 40/67 |
| 11,540,757 B2 | 1/2023 | Kuenen | |
| 2004/0147817 A1* | 7/2004 | Dewing | G16H 50/20 |
| | | | 128/923 |
| 2008/0306763 A1* | 12/2008 | James | G16H 40/67 |
| | | | 705/2 |

(Continued)

FOREIGN PATENT DOCUMENTS

AU 2018260916 A1 11/2018

OTHER PUBLICATIONS

N. Jamalian, M. Gillies, F. F. Leymarie and X. Pan, "The Effects of Hand Tracking on User Performance: an experimental study of an object selection based memory game," 2022 IEEE Intl Sym on Mixed and Augmented Reality (ISMAR), Singapore, Singapore, 2022, pp. 768-776, doi: 10.1109/ISMAR55827.2022.00095 (Year: 2022).*

(Continued)

*Primary Examiner* — Sun M Li
(74) *Attorney, Agent, or Firm* — Lily Neff (57) ABSTRACT

A method, computer system, and a computer program product are provided for testing functional mobility and memory. Information is about a participant to an artificial intelligence (AI) engine and then instructions are provided to the participant to memorize a random set of steps. The participant is then asked to recall the random set of instruction steps and then to perform the steps memorized. The participant is asked to recall the steps again after the physical performance. The result of the test is analyzed and a final participant assessment is rendered based on the overall performance analysis. The participant is provided instructions and further monitored and recorded for the performance of the test using smart devices, video or similar means.

17 Claims, 5 Drawing Sheets

(56) References Cited

U.S. PATENT DOCUMENTS

| | | | |
|---|---|---|---|
| 2014/0067730 A1* | 3/2014 | Kozloski | G16H 20/70 |
| | | | 706/12 |
| 2014/0276130 A1* | 9/2014 | Mirelman | A61B 5/1104 |
| | | | 600/595 |
| 2017/0270818 A1 | 9/2017 | French | |
| 2019/0125240 A1 | 5/2019 | Michel | |
| 2020/0258631 A1 | 8/2020 | Baker | |
| 2020/0327989 A1* | 10/2020 | Kuenen | A61B 5/16 |
| 2020/0365275 A1* | 11/2020 | Barnett | G10L 25/63 |
| 2022/0036752 A1 | 2/2022 | Gazzaley | |
| 2022/0202373 A1* | 6/2022 | Yocca | A61B 5/4035 |
| 2023/0307116 A1* | 9/2023 | Mahulikar | G16H 40/67 |

OTHER PUBLICATIONS

Wirzberger M, Schmidt R, Georgi M, Hardt W, Brunnett G, Rey GD. Effects of system response delays on elderly humans' cognitive performance in a virtual training scenario. Sci Rep. Jun. 5, 2019;9(1):8291. doi: 10.1038/s41598-019-44718-x. PMID: 31165754; PMCID: PMC6549173. (Year: 2019).*

Buszard T, Farrow D, Verswijveren SJJM, Reid M, Williams J, Polman R, Ling FCM, Masters RSW. Working Memory Capacity Limits Motor Learning When Implementing Multiple Instructions. Front Psychol. Aug. 22, 2017;8:1350. doi: 10.3389/fpsyg.2017.01350. PMID: 28878701; PMCID: PMC5572292. (Year: 2017).*

Scientists' Perspectives on the Potential for Generative AI in their Fields, by Meredith Ringel Morris, Google Research, arXiv:2304.01420v1 [cs.CY] Apr. 4, 2023 (Year: 2023).*

Cekok, et al., "Timed Up and Go Test With a Cognitive Task: Correlations With Neuropsychological Measures in People With Parkinson's Disease", Cureus 12(9): e10604, Sep. 22, 2020, 7 pgs., <https://www.ncbi.nlm.nih.gov/pmc/articles/PMC7584288/>.

Lima, et al., "The Relationship Between Dual-task and Cognitive Performance Among Elderly Participants Who Exercise Regularly", Braz J Phys Ther., Mar.-Apr. 2015; 19(2): pp. 159-166, <https://www.scielo.br/j/rbfis/a/qRmzNFwyDfp8RxwNTncDDgm/?lang=en&format=pdf>.

Van Patten, et al., "The Utility of the Timed Up-and-Go Test in Predicting Cognitive Performance: A Cross-Sectional Study of Independent Living Adults in a Retirement Community", Journal of Applied Gerontology, 39(10), Oct. 1, 2020, 14 pgs., <https://escholarship.org/uc/item/1kw2z188>.

* cited by examiner

REMOTE CONCURRENT ASSESSMENT OF FUNCTIONAL MOBILITY AND WORKING MEMORY

BACKGROUND

The present invention relates generally to the field of data management and more particularly to techniques for remote behavioral assessments.

Pursuant to the observed escalation in life expectancies, a corresponding augmentation in the prevalence of conditions predominantly impacting the elderly demographic has been documented. In consideration of the necessity to accommodate the needs of said aging population, as well as individuals who may experience analogous afflictions regardless of their advanced age, various diagnostic assessments and telecommunication-based behavioral support applications (hereinafter referred to as "apps") have been devised and implemented. A significant proportion of these apps encompasses measures that address the management and mitigation of neurodegenerative diseases.

One assessment for diagnosing neurodegenerative conditions has to do with requiring the patient to perform more than one task at the same time. For instance, a participant may be asked to perform a physical task concurrently with a cognitive task, which has been found to correlate well with neuropsychological measures in elderly or people suffering from neurodegenerative diseases. Studies have found that these types of multi-task tests may be a powerful predictor of longitudinal progression of certain diseases. There seems to be a strong correlation between physical and cognitive decline in the elderly and others suffering from certain conditions.

SUMMARY

Embodiments of the present invention disclose a method, computer system, and a computer program product for testing functional mobility and memory of a person. Information is acquired about a patient or a participant of a test using an artificial intelligence (AI) engine. A sequence of random instructions is then provided to the patient/participant and later asked to be recalled by the patient/participant. The patient/participant is then asked to perform the instructions physically. The patient/participant is then asked again to recall the steps from memory without performing them physically. The results of the patient/participant performance are then analyzed. In one embodiment, a final participant assessment is rendered based on an overall performance analysis. In one embodiment, the patient/participant is provided random set of instructions and further monitored and recorded for the performance analysis using a smart device and/or through use of audio/video recording using sensors or similar means.

BRIEF DESCRIPTION OF THE SEVERAL VIEWS OF THE DRAWINGS

These and other objects, features and advantages of the present invention will become apparent from the following detailed description of illustrative embodiments thereof, which may be to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods may be disclosed herein; however, it can be understood that the disclosed embodiments may be merely illustrative of the claimed structures and methods that may be embodied in various forms. This invention may, however, be embodied in many different forms and should not be construed as limited to the exemplary embodiments set forth herein. Rather, these exemplary embodiments may be provided so that this disclosure will be thorough and complete and will fully convey the scope of this invention to those skilled in the art. In the description, details of well-known features and techniques may be omitted to avoid unnecessarily obscuring the presented embodiments.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Figure 1:
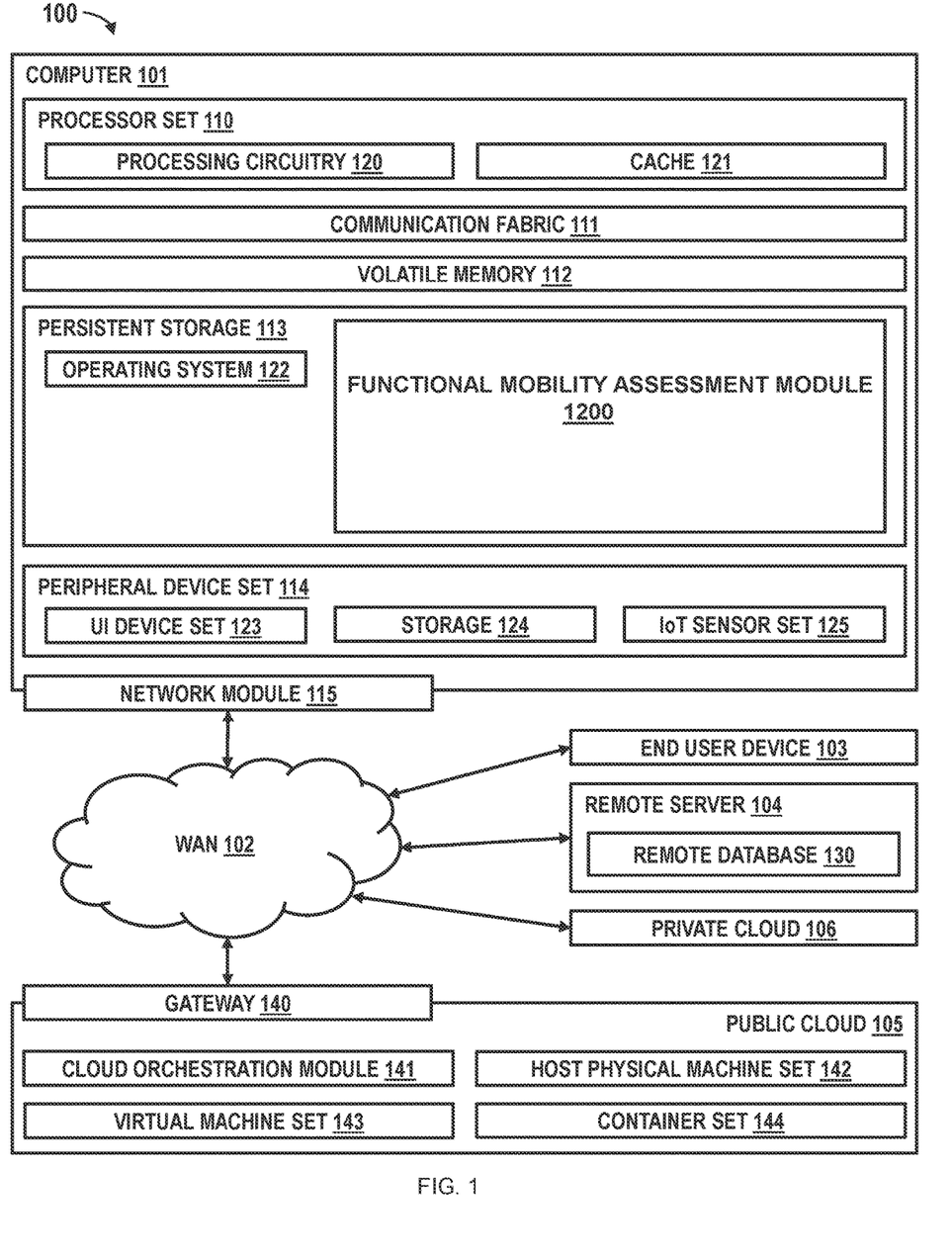
FIG. 1 illustrates a networked computer environment, according to at least one embodiment.

FIG. 1 provides a block diagram of a computing environment 100. The computing environment 100 contains an example of an environment for the execution of at least some of the computer code involved in performing the inventive methods, such as code change differentiator which is capable of providing Functional Mobility Assessment Module (1200). In addition to this block 1200, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 1200, as identified above), peripheral device set 114 (including user interface (UI), device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 of FIG. 1 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 1200 in persistent storage 113.

COMMUNICATION FABRIC 111 is the signal conduction paths that allow the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, the volatile memory is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and rewriting of data. Some familiar forms of persistent storage include magnetic disks and solid state storage devices. Operating system 122 may take several forms, such as various known proprietary operating systems or open source Portable Operating System Interface type operating systems that employ a kernel. The code included in block 1200 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion type connections (for example, secure digital (SD) card), connections made though local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers.

A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

Figure 2:
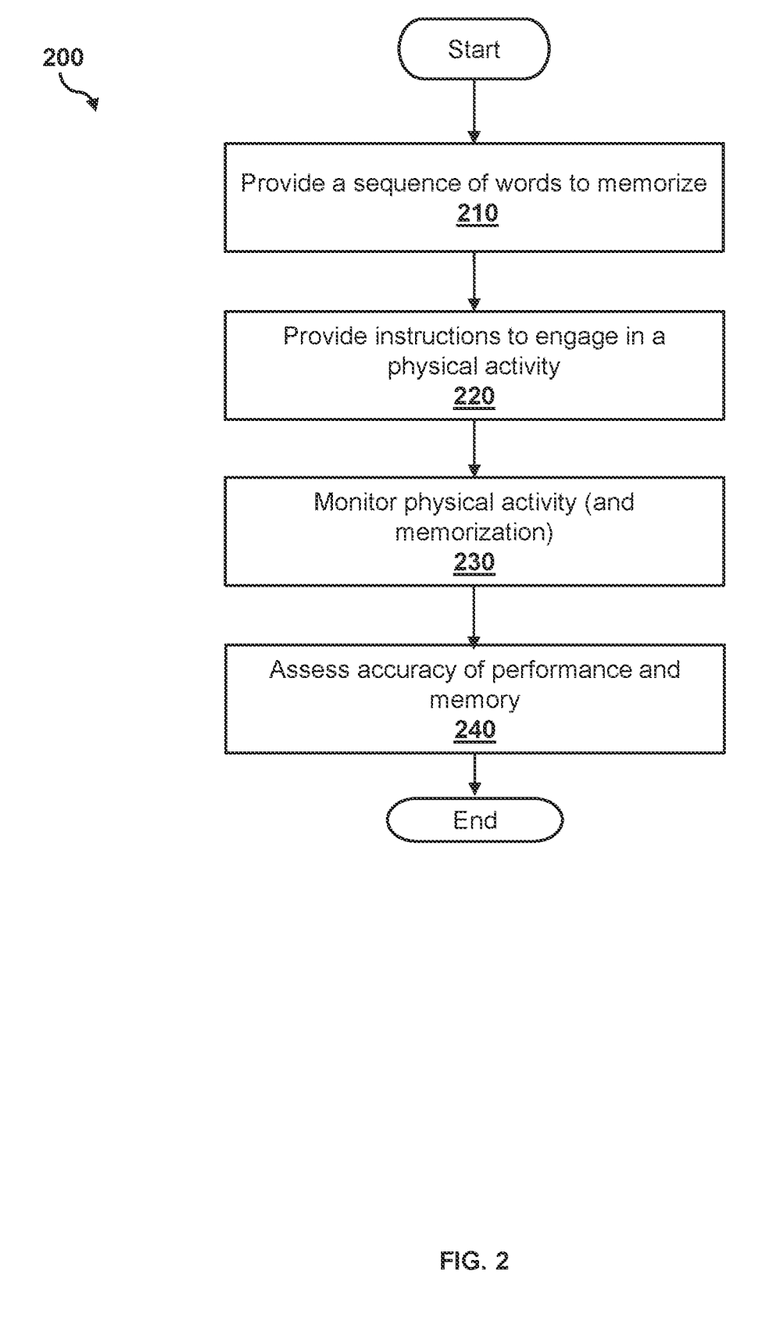
FIG. 2 provides an operational flowchart used for testing memory and mobility of a patient/participant, according to one embodiment.

FIG. 2 provides a functional memory and mobility assessment process 200. As discussed earlier, dual task tests require a patient/participant to perform more than one task at the same time. For instance, a patient/participant may be asked to perform a physical task concurrently with a cognitive task, which has been found to correlate well with neuropsychological measures in elderly or people suffering from neurodegenerative diseases. For example, a Timed Up and Go (hereinafter TUG) cognitive dual task test may be a combined cognitive task often administered to the elderly. Subjects may be asked to sit in a chair, stand up, walk a few feet, turn around, walk back to the chair and sit down. At the same time, they need to perform a cognitive task requiring one to count backwards by three (reverse digit span). Studies have found that this test may be a powerful predictor of longitudinal progression of some neurodegenerative diseases such as Parkinson's disease. There seems to be a strong correlation between physical and cognitive decline especially in the elderly which justifies a concurrent approach to measuring them.

Process 200 provides an easy to implement solution that can be incorporated in a variety of devices. For example, for ease of convenience, the process 200 can be implemented on a mobile device as a mobile application (app). It may even be administered remotely without the supervision of a clinician using mobile devices. I can also use nearby sensors and audio/video components to implement it. Streaming of the performance can also be possible.

The test may be automated using machine language modules and be self-learning. An artificial intelligence (AI) engine can be used to teach machine learning modules. Parts of the test can also incorporate the help of researchers, physicians, caregivers or other third parties.

In addition, prior user history (such as by a user profile can also be used) of the same patient/participant or other patient/participants with similar conditions or without the particular condition can be used to present instructions and analyze the results ultimately through comparison etc.

In addition, in one embodiment, when a third party has to be incorporated into the test a Tester Instruction, Tester Worksheet and Subject Instruction can be provided and incorporated into the sequence generated or the time determined to complete the test. In one embodiment, the Tester Instruction (as provided to the AI or by the AI) may contain detailed steps of how to administer the test. In addition, the Tester Worksheet may contain a form for a researcher/clinician to be later provided so that observations can be provided in connection with each patient in an organized format. In addition, if there may be one or more people helping with the administering of the test, Subject Instruction, such as through an email, text or even a hand-out can be provided to help researcher/clinician to explain the process to the test subject.

The process 200, as will be discussed, tests for a concurrent memory and physical element. For example, a physical task that may be specifically targeted to the patient/participant or a condition needs to be provided simultaneously with a memory element that may be relative to other cognitive features. In FIG. 2 process 200 provides a first embodiment of such an assessment. In one embodiment, this process may be referenced as a Pace Turn Test.

In Step 210, a sequence of instructions may be provided to a patient/participant for memorization. The sequence may be provided in a variety of manners or through one or more devices. For example, for convenience, in this embodiment, the test may be implemented on a smart device such as a smartphone or smartwatch or other similar types of smart wearable device.

In one embodiment, using a mobile app connected with the smart device, the test can be administered and used for data collection to assess a final result. This allows for the test to be administered remotely, even through interconnected devices, and without a need for human supervision (no clinicians needed) unless desired.

In one embodiment, the test can be administered and re-administered iteratively as needed over time through the use of Artificial Intelligence (AI) and machine learning component that learns more about the abilities of the participant/patient. Therefore, the test can take previous level of ability of the patient/participant into consideration and provide an appropriate follow up test to determine an improvement or worsening of the patient/participant condition.

In Step 220, further instructions may be provided to the patient/participant accordingly for a series of physical activity to be performed. In one embodiment, the physical component and the sequence of instructions provided for memorization may be corresponding. For example, in this example, the patient/participant may be provided with a random sequence of the words "Left" and "Right" and maybe even "Turn" (Step 210) in a particular repeated manner. In this way the order of how the Left and Right appears first tests the memory and then becomes part of a physical activity to be performed by the patient/participant. In the physical portion, the patient/participant may have to pace back and forth in a designated area and make turns according to the sequence.

In Step 230, the performance of the activity may be monitored by the AI through the device etc. In one embodiment, sensors can be provided for data collection and storage connected with the test. In one example, sensors may be already incorporated into the smart device such as mobile phones or watches. These sensors can adequately monitor and record the movements performed during the test. Other sensors can also be incorporated that measure other health factors if desired (heart rate, temperature etc.). In one example, the process when implemented on a smartphone or smartwatch app may take advantage of the built-in gyroscope and accelerometer to automatically assess the accuracy of the turns and mobility features. In other embodiment, audio and video captures and image-based data may be gathered in lieu or in addition to the sensor information.

In Step 240, the accuracy of performance of the instructions may be provided through analysis of data collected (sensor data etc.). Assessing accuracy of two or more types of abilities at the same time (multitasking) may be important as discussed. The concurrent element to the physical task specifically targets working memory relative to other cognitive features. Studies have shown that memory impairment correlates with physical impairment in the elderly. Assessing two (or more) types of abilities at the same time (multitasking) may be unique because having to perform two tasks at once can be more cognitively taxing. This increases the likelihood of exposing deficit or decline that may otherwise be masked in a single task through cognitive reserve or strategy use.

Figure 3:
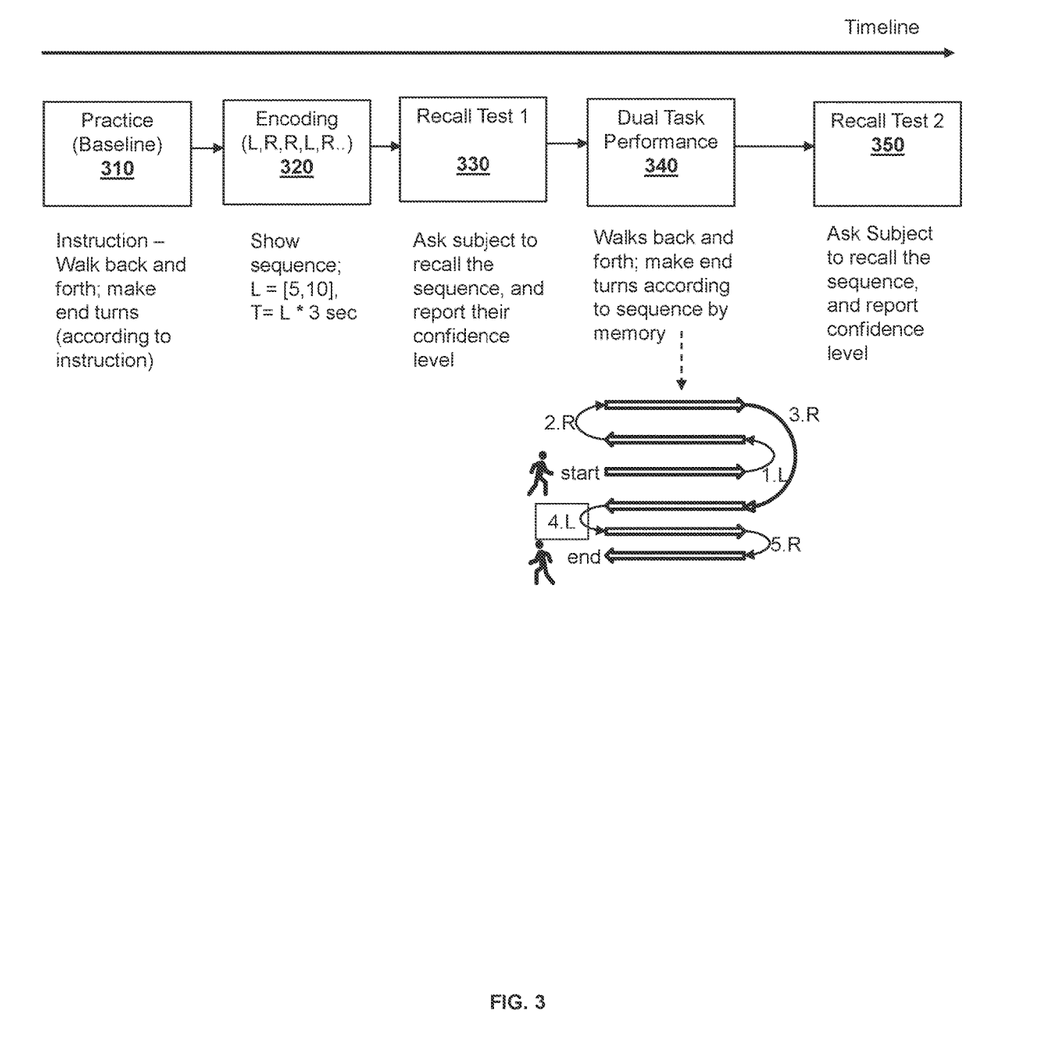
FIG. 3 provides a block diagram of a timeline of the testing such as that provided through the process of FIG. 2, according to one embodiment.

FIG. 3 provides a block diagram of a timeline for performing the steps of process 200 of FIG. 2 according to a specific scenario to provide ease of understanding. In this scenario, as reflected by 310 a practice step may be provided to establish a baseline. In this example, the test taker (patient/participant) may be provided a simple activity to provide a baseline measure. In this example, the baseline activity may be a walk such as one that includes back and forth pacing and turning at the end of a walkway according to the instructions or an AI type command (could also be provided remotely by a person, a video recording etc.).

In block 320, a sequence may be encoded to be provided to the patient/participant. For way of example, this may be "Left, Right, Right, Left, Right . . . " as shown in the figure. This will correspond to a sequence having a length of a walk and an expected time to complete it that may correspond to the baseline performance or some other metric such as previous performance of the patient or an expected metrics for a healthy person. This is shown in this example as the sequence Length=[5,10] and time t=L*3.

In block 330, a first recall test may be performed (Recall Test 1). In this scenario, the patient/participant may be asked to recall the sequence of words provided. In one embodiment, the patient/participant may also be asked to report their confidence in recalling the sequence.

In block 340, the patient/participant may be instructed to perform the dual task. This will include, in this example, for the patient/participant to walk back and forth and make end turns accordingly while recalling the sequence from memory.

In block 350, Recall Test 2 may be administrated that asks the subject to recall the sequence. In one embodiment, the patient/participant may also be asked to reflect on their accuracy confidence level of having performed the test correctly.

In this scenario, a variety of components that are associated with a participant/patient mobile device, or wearable or some other combination can be used in helping with each block (step) of the process. For example, an accelerometer can be used for counting steps, measuring hand swinging, average linear acceleration. A gyroscope can be used for determining turnings, measuring total turning angle, angular velocity, angular acceleration. Video/audio can be used for determining gait balance, step counts, hand swinging, quantify mobility features like stride length, step speed and etc. Video/audio can also provide information on hesitation and other cognitive aspects. Data stream associated with all the methods discussed may also be used to determine turning time, walking time and other movements. In addition, memory analysis may be performed based on the recall of correct sequences (in recalling—Tests 1 and 2), trials to correct sequence in recall tests 1 and 2, and recall of sequences during TUG. Both reaction time and accuracy may be assessed for each measure.

Figure 4:
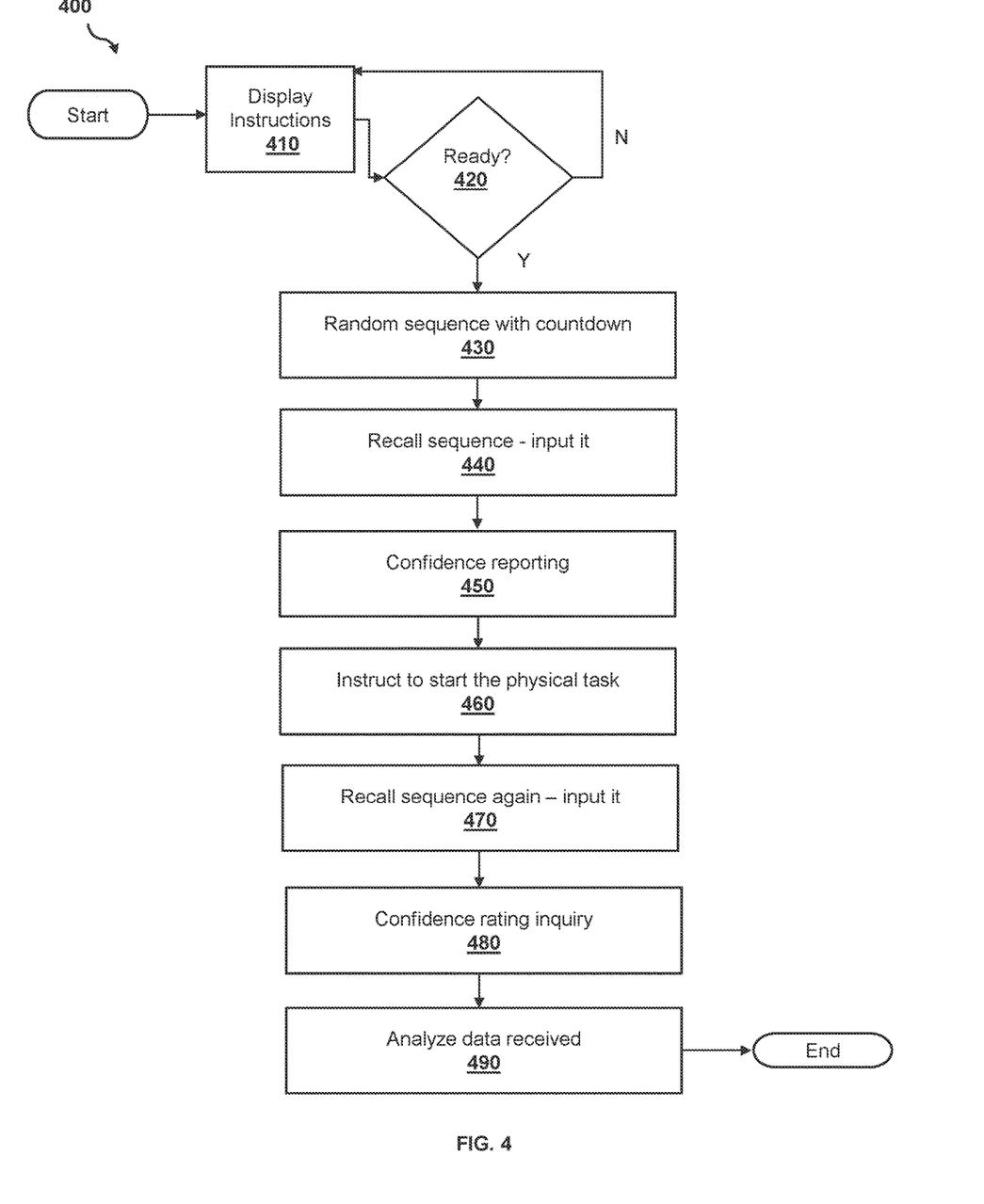
FIG. 4 provides an operational flowchart for an alternate embodiment providing a testing technique for memory and mobility, according to one embodiment.

FIG. 4 provides a flowchart illustration of another embodiment through process 400 that is similar to process 200 of FIG. 2. In Step 410, the instruction may be provided to the test participant (patient etc.). A variety of different scenarios can be used as the way the instruction is provided. For example, the test, in one embodiment, can be provided through a wearable device such as a smartwatch, glasses etc. In one embodiment, a practice session can be even performed to establish base lines for the actual test.

In Step 420, it may be also determined when the subject or participant of the test may be ready to perform the test. This can be conducted by asking the participant (patient) or a third person such as a doctor or a caregiver who may be monitoring the subject either in person or remotely through a device. The readiness can be also ascertained through the use of the AI engine.

In one embodiment, alternate arrangements can be made. For example, the test can be carried out by providing instruction via a smartphone application or even in paper form, while collecting data may be performed with the help of a video system that records or even livestreams the participants performance.

In Step 430, a random sequence may be provided to the participant. The sequence can be provided through a variety of methods such as through the smart device, on video, on paper etc. as can be appreciated by those skilled in the art. In one embodiment, a countdown timer can be instigated as well to measure the time it takes to memorize or understand the instruction by the participant. The timer can be used to assess the condition of the participant and/or setup a basis for later assessments in future tests. In one embodiment, the timer can be used to provide a time frame for the entirety of the process/test or be stopped and started during each step (or a combination can be used) to measure the participants overall or incremental performance of each step.

In Step 440, the participant will recall the sequence. The recall can be made in a variety of ways. In one embodiment, for example, the participant can type the sequence as an input into the smart device. In another embodiment, the input can be provided orally and recorded on video. It can also be provided via a live stream using one or more devices and sensors. These are only a few examples and other ways can be incorporated into alternate embodiments.

In one embodiment a follow up step may be provided that may be optional. In this step as illustrated in Step 450, the participant may be asked to provide their confidence level in their recall of the sequence. Again, this can be reported by the participant orally or by inputting a response.

In Step 460, the participant may be instructed to start performing the physical portion of the test. The instruction can be provided in a number of ways such as those discussed earlier. Once the participant starts performing the physical portion (walking, turning etc.), the performance may be monitored and in one embodiment recorded. The data collection (performance monitoring and recording) can be performed using a number of sensors disposed nearby or through a video or streaming device. When a smart device is being used, the sensors and other needed components (accelerometers, gyroscopes etc.) already incorporated into the smart device can be used.

In Step 470, the participant may be asked to recall the sequence of the instructions and provide it by entering it or recalling it back orally using a number of manners available to the participant (subject).

In Step 480, the participant can be asked again (optionally) to provide a confidence level associated with the physical performance of the task provided in Step 460.

In Step 490, the results of the performance may be analyzed using the obtained data (through streaming, smart device video etc.).

Figure 5:
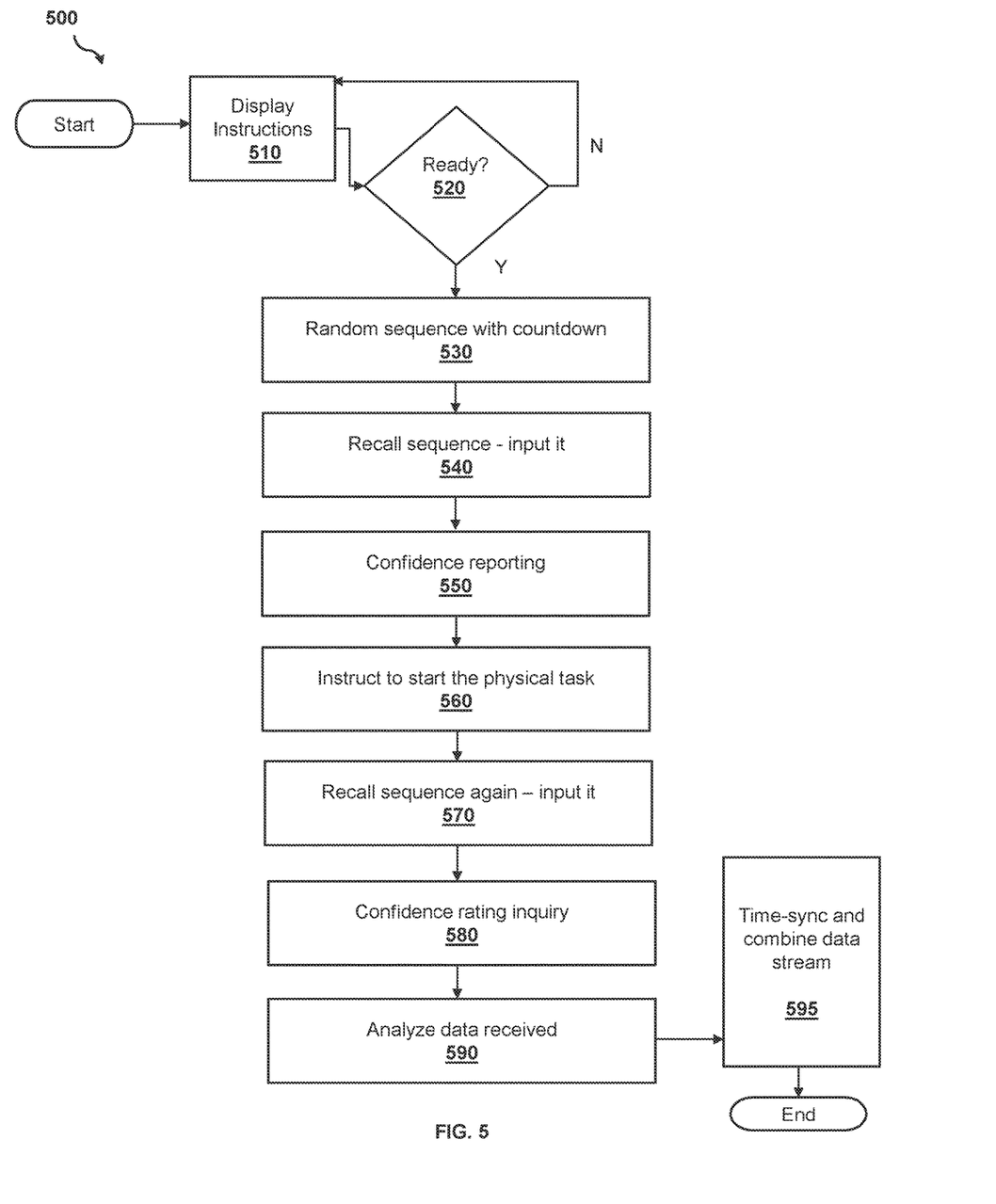
FIG. 5 provides an operational flowchart of a mobility and memory testing technique with multiple synchronized data gathering components, according to one embodiment.

FIG. 5 provides a similar embodiment to that of FIG. 4. The process 400 may be similar to process 500 except in FIG. 5 (process 500) the test may be carried out by providing a recording using two different methods. For example, in one embodiment the instructions are provided to the participant (Step 510) using any method but then once the participant is ready (Step 520), the following steps 530 to 590 may be provided in the same manner but the response data, may be collected using at least two methods. In this scenario the two methods are through the use of a smart device and video recording.

In Step 595, the two data collection methods may be time synchronized with one another and combined as two data streams to provide a combined score with a better measure of the subject performance.

In one embodiment a final participant assessment may be performed such as by the AI engine or other means to provide an overall performance analysis. The final participant assessment, for example, can include a comparison of a previous assessment by the same participant. Other factors can also be taken into consideration. For example, there may be a scoring where the working memory may be scored based on how accurate some element (i.e., the turns) are performed during a walk compared to the original sequence (left and right). The countdown and the time of task performance may also be analyzed against the participant's previous performance (if one exists) or against some other participants or predetermined measures. Mobility may similarly be scored using standard approaches such as its relationship specific to one or more conditions or diseases that may be in question.

In one embodiment, the final assessment analysis can be stored for future assessment of this particular participant or to be used for other participants in the similar condition (same age, same disease prognosis etc.).

The descriptions of the various embodiments of the present invention have been presented for purposes of illustration but may be not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for testing functional mobility and memory, comprising:
   providing information about a participant to an artificial intelligence (AI) engine to train the AI to provide instructions to a participant based on participant user history and a participant particular health condition, wherein said artificial intelligence engine uses a plurality of sensors to assess accuracy of a participant performance;
   assessing said information using said AI engine and training a machine learning module to provide instructions to said participant to memorize a random set of steps to be performed physically, wherein said random set is designed to meet at meet a set of conditions extracted from said assessed information about said participant, wherein said participant is instructed to provide a confidence assessment after performing a memory recall of said random set of instructions and said confidence assessment is used as part of an overall performance assessment;
   inquiring from said participant to recall said random set of instructions without performing them physically and said AI engine assessing recall accuracy;
   providing a set of random instructions to said participant to perform using said AI engine and said machine learning module, wherein said set of instructions have a physical instruction component and a non-physical memory component to be completed simultaneously;
   instructing said participant to perform said random set of instructions as a sequence of steps physically assessing the recall and performance accuracy, wherein said participant is instructed to provide a confidence assessment after performing said physical performance of said instructions;
   analyzing by said AI engine the cognitive ability participant through performance of simultaneously memory and physical features as a determination for cognitive condition;
   analyzing by said AI engine the overall performance of said participant and determining a current state of physical and mental capacity of said participant based on an overall analysis; and
   providing a final participant assessment by said AI engine based on said overall performance analysis.

2. The method of claim 1, wherein said artificial intelligence engine records said overall performance analysis and said final participant assessment.

3. The method of claim 2, wherein said final participant assessment is used to provide another set of random sequence of instructions for a future test for said participant.

4. The method of claim 3, wherein an original participant assessment is generated to provide another set of random sequence of instructions for a future test to a different participant having a condition similar to said participant.

5. The method of claim 1, wherein a previous assessment of at least one condition associated with said participant is obtained.

6. The method of claim 5, wherein a recorded final participant assessment is generated to determine if said at least one condition associated with said participant is improving or deteriorating.

7. The method of claim 1, wherein said instruction provided participant is instructed to provide a confidence assessment after performing said physical performance of said instructions and said confidence assessment is used as part of the overall performance assessment instructions.

8. The method of claim 1, wherein said instructions are provided using a mobile device and said sensors are provided in said mobile device.

9. The method of claim 1, wherein said instructions are provided using a wearable device and said sensors are provided in said wearable device.

10. The method of claim 1, wherein said overall performance assessment results are sent to a third person monitoring said participant's condition.

11. A computer system for testing functional mobility and memory, comprising:
    one or more processors, one or more computer-readable memories and one or more computer-readable storage media;
    program instructions, stored on at least one of the one or more storage media for execution by at least one of the one or more processors via at least one of the one or more memories, to provide information about a participant to an artificial intelligence (AI) engine to train the AI to provide instructions to a participant based on participant user history and a participant particular health condition, wherein said artificial intelligence engine uses a plurality of sensors to assess accuracy of a participant performance;
    program instructions, stored on at least one of the one or more storage media for execution by at least one of the one or more processors via at least one of the one or more memories, to assess by said AI engine said information and train a machine learning module to provide instructions to a participant to memorize a random set of steps to be performed physically, wherein said random set is designed to meet at meet a set of conditions extracted from said assessed information about said participant, wherein said participant is instructed to provide a confidence assessment after performing a memory recall of said random set of instructions and said confidence assessment is used as part of an overall performance assessment;

program instructions, stored on at least one of the one or more storage media for execution by at least one of the one or more processors via at least one of the one or more memories, to inquire from said participant to recall said random set of instructions without performing them physically and said artificial intelligence assessing the recall accuracy;

program instructions, stored on at least one of the one or more storage media for execution by at least one of the one or more processors via at least one of the one or more memories, to provide a set of random instructions to said participant to perform using said Al engine and said machine learning module, wherein said set of instructions have a physical instruction component and a non-physical memory component to be completed simultaneously;

program instructions, stored on at least one of the one or more storage media for execution by at least one of the one or more processors via at least one of the one or more memories, to instruct said participant to perform said random sequence of steps physically and said Al engine assessing the participant recall and performance accuracy;

program instructions, stored on at least one of the one or more storage media for execution by at least one of the one or more processors via at least one of the one or more memories, to analyze by said Al engine the cognitive ability participant through performance of simultaneously memory and physical features as a determination for cognitive condition;

program instructions, stored on at least one of the one or more storage media for execution by at least one of the one or more processors via at least one of the one or more memories, to analyze said overall performance of said participant and determining a current state of physical and mental capacity of said participant based on overall analysis; and program instructions, stored on at least one of the one or more storage media for execution by at least one of the one or more processors via at least one of the one or more memories, to provide a final participant assessment based on said overall performance analysis.

12. The computer system of claim 11, wherein said artificial intelligence engine records said overall performance analysis and said final participant assessment.

13. The computer system of claim 12, wherein a previous assessment of at least one condition associated with said participant is obtained.

14. The computer system of claim 12, wherein said final participant assessment is used to provide another set of random sequence of instructions for a future test for said participant.

15. The computer system of claim 14, wherein said original participant assessment is used to provide another set of random sequence of instructions for a future test to a different participant having a condition similar to said participant.

16. The computer system of claim 11, wherein said instruction provided participant is instructed to provide a confidence assessment after performing said physical performance of said instructions and said confidence assessment is used as part of the overall performance assessment instructions.

17. A computer program product for testing functional mobility and memory, the computer program product comprising:

one or more computer readable storage media;

program instructions, stored on at least one of the one or more storage media for execution by at least one of the one or more processors via at least one of the one or more memories, to provide information about a participant to an artificial intelligence (AI) engine to train the Al to provide instructions to a participant based on participant user history and a participant particular health condition, wherein said artificial intelligence engine uses a plurality of sensors to assess accuracy of a participant performance;

program instructions, stored on at least one of the one or more storage media for execution by at least one of the one or more processors via at least one of the one or more memories, to assess by said Al engine said information and train a machine learning engine module to provide instructions to a participant to memorize a random set of steps to be performed physically; wherein said random set is designed to meet at meet a set of conditions extracted from said assessed information about said participant, wherein said participant is instructed to provide a confidence assessment after performing a memory recall of said random set of instructions and said confidence assessment is used as part of an overall performance assessment;

program instructions, stored on at least one of the one or more storage media for execution by at least one of the one or more processors via at least one of the one or more memories, to inquire from said participant to recall said random set of instructions without performing them physically and said artificial intelligence assessing the recall accuracy;

program instructions, stored on at least one of the one or more storage media for execution by at least one of the one or more processors via at least one of the one or more memories, to provide a set of random instructions to said participant to perform using said Al engine and said machine learning module, wherein said set of instructions have a physical instruction component and a non-physical memory component to be completed simultaneously;

program instructions, stored on at least one of the one or more storage media for execution by at least one of the one or more processors via at least one of the one or more memories, to instruct said participant to perform said random sequence of steps physically and said Al engine assessing the participant recall and performance accuracy;

program instructions, stored on at least one of the one or more storage media for execution by at least one of the one or more processors via at least one of the one or more memories, to analyze by said Al engine the cognitive ability participant through performance of simultaneously memory and physical features as a determination for cognitive condition;

program instructions, stored on at least one of the one or more storage media for execution by at least one of the one or more processors via at least one of the one or more memories, to analyze said overall performance of said participant and determining a current state of physical and mental capacity of said participant based on overall analysis; and program instructions, stored on at least one of the one or more storage media for execution by at least one of the one or more processors via at least one of the one or more memories, to provide a final participant assessment based on said overall performance analysis.

* * * * *